United States Patent [19]

Ezrailson

[11] Patent Number: 5,385,825
[45] Date of Patent: Jan. 31, 1995

[54] COMPOSITION FOR PROCESSING BODYFLUIDS, METHOD OF PROCESSING BODYFLUIDS AND PRODUCTS MADE FROM BODYFLUIDS

[75] Inventor: Edward G. Ezrailson, The Woodlands, Tex.

[73] Assignee: Emerald Biomedical Sciences, Inc., The Woodlands, Tex.

[21] Appl. No.: 94,512

[22] Filed: Jul. 20, 1993

[51] Int. Cl.⁶ .................. G01N 33/574; G01N 1/00; C12N 9/00; C12Q 1/37

[52] U.S. Cl. .................. 435/7.23; 435/2; 435/4; 435/23; 435/183; 435/962; 435/963; 435/7.1; 435/7.2; 435/7.4

[58] Field of Search .......... 436/8; 435/2, 4, 23, 435/24, 183, 962, 963, 7.23, 7.1, 7.2, 7.4

[56] References Cited

U.S. PATENT DOCUMENTS

| | | | |
|---|---|---|---|
| 4,301,028 | 11/1981 | Bartl et al. | 436/8 |
| 4,409,334 | 10/1983 | Lill et al. | 436/8 |
| 4,962,038 | 10/1990 | Carter et al. | 436/8 |
| 5,008,202 | 4/1991 | Edmondson et al. | 436/8 |
| 5,021,342 | 6/1991 | Greene et al. | 435/91 |
| 5,094,956 | 3/1992 | Grow et al. | 436/8 |

OTHER PUBLICATIONS

Biochemica Information, First Edition, Compiled and Edited by Joseph Keesey, Ph.D., Published by Boehringer Mannheim Biochemicals (1987), pp. 106, 107, 111, 121–123.

*Primary Examiner*—Toni R. Scheiner
*Attorney, Agent, or Firm*—Gilbreth & Adler

[57] ABSTRACT

Disclosed is a composition useful in the processing of blood and cerebrospinal fluid to help maintain sample integrity for analytical testing. The composition generally includes a first enzyme inhibitor selected from the group of enzyme inhibitors consisting of inhibitors which allow substantially the function of metalo-peptidase while inhibiting at least one enzyme selected from the group of enzymes consisting of endopeptidase, exopeptidase and sulfhydryl-mediated proteases, and inhibitors which substantially inhibit the function of metalo-peptidase, wherein where the first enzyme inhibitor inhibits metalo-peptidase, the assaying composition further comprises a second enzyme inhibitor suitable to inhibit at least one enzyme selected from the group of enzymes consisting of endopeptidase, exopeptidase, metalo-peptidase and sulfhydryl-mediated proteases. Further disclosed is an apparatus which includes a tube containing the inhibitors into which the bodyfluids are placed. In the method, blood or cerebrospinal fluid is contacted with the inhibitors prior to analytical testing. Also disclosed are products of the bodyfluids and inhibitors which are useful for analytical testing.

44 Claims, 1 Drawing Sheet

U.S. Patent    Jan. 31, 1995    5,385,825
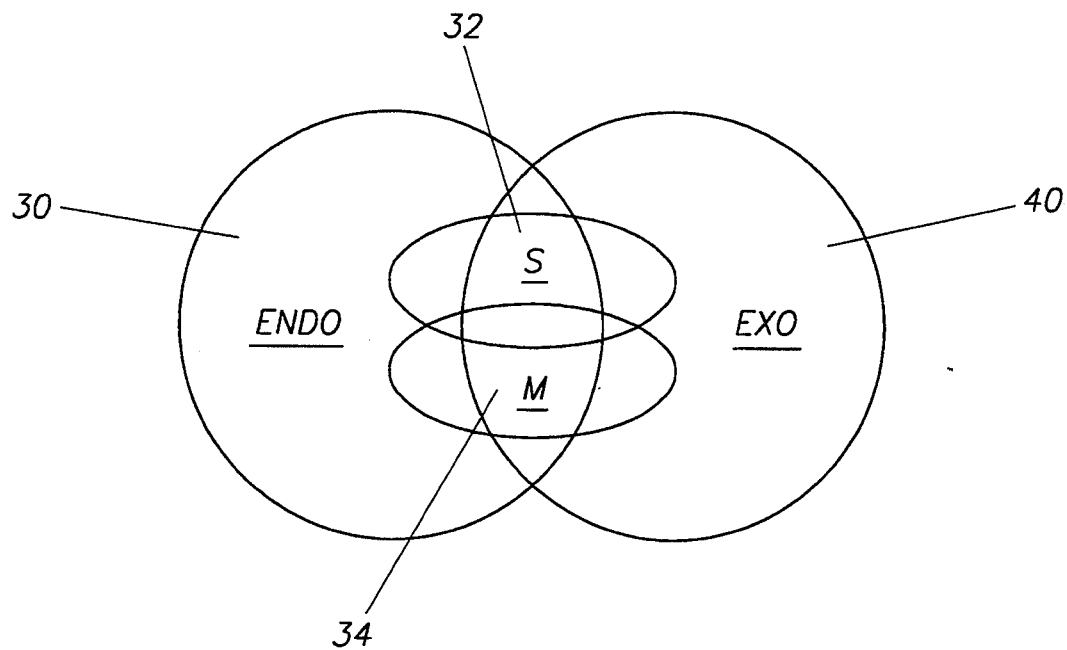
FIG.1
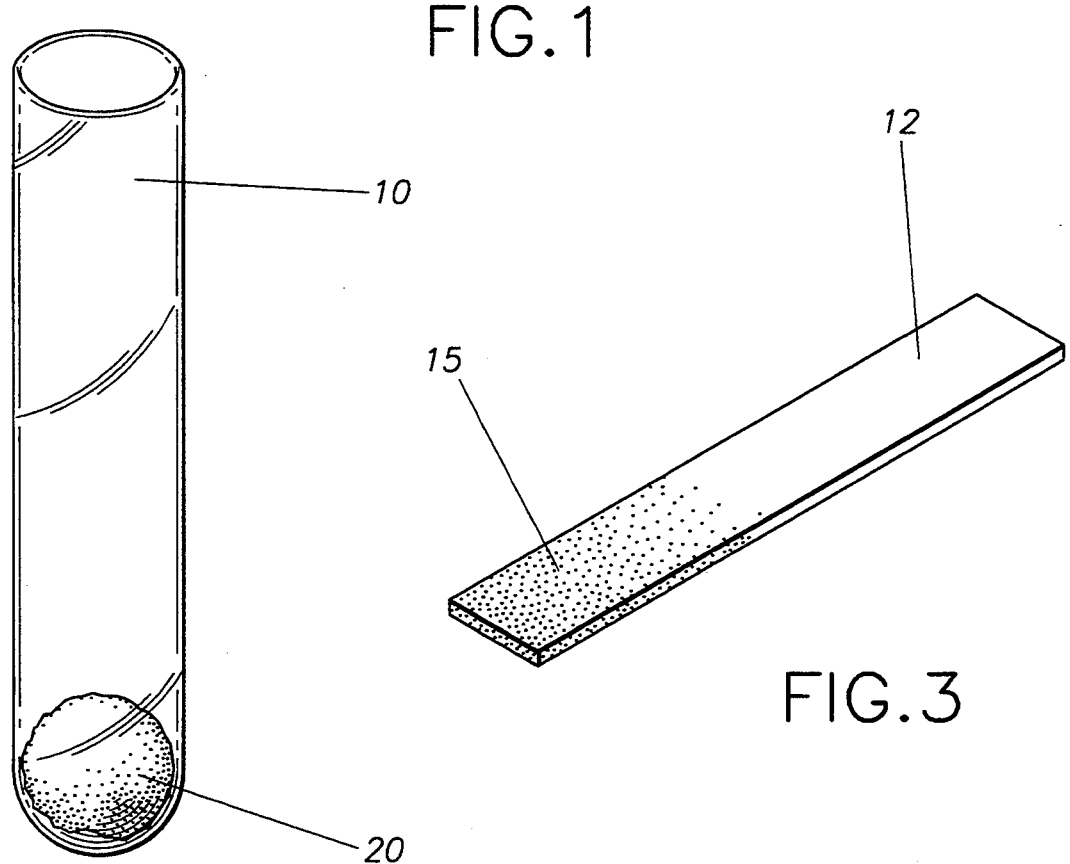
FIG.2
FIG.3

COMPOSITION FOR PROCESSING BODYFLUIDS, METHOD OF PROCESSING BODYFLUIDS AND PRODUCTS MADE FROM BODYFLUIDS

BACKGROUND OF THE INVENTION

1. Field of the Invention

The present invention relates to a composition for processing bodyfluids, an apparatus for processing bodyfluids, a method of processing bodyfluids and to products made from bodyfluids. In another aspect, the present invention relates to a composition of enzyme inhibitors for processing blood and cerebrospinal fluid, to an apparatus made of enzyme inhibitors for processing blood and cerebrospinal fluid, to a method of processing cerebrospinal fluid and blood utilizing enzyme inhibitors, and to products made from cerebrospinal fluid or blood.

2. Brief Description of the Related Art

Biological bodyfluids, such as cerebrospinal fluid, blood, amniotic fluid, and other fluids, are routinely removed from humans and other animals and subjected to analytical testing. Such analytical testing is useful for diagnosing and treating diseases, conditions and other pathologies.

Since such analytical testing will be used for medical diagnosis and treatment, accurate test results are obviously very necessary and important. Unfortunately, once bodyfluids are drawn they can undergo degradative, catabolic, anabolic or other processes which may alter the outcome of the test results so that they are not reflective of actual body conditions. To ensure proper and accurate test results, it is important that the integrity of such bodyfluids be maintained so that the test results are reflective of actual body conditions.

Generally, to maintain the integrity of a bodyfluid sample, analytical testing is performed as soon after sampling as possible, or it is refrigerated or frozen with the test to be performed at a later time as soon after thawing as possible.

While it is most desirable to conduct analytical testing promptly after the bodyfluid is drawn, the practical reality is that analytical testing is not always performed as promptly as is desired. Additionally, with time consuming test procedures, the integrity of the bodyfluid can also be compromised during the testing procedure.

Another practical reality is that many physician's offices and smaller laboratories, lack the ability to conduct all but the most simple of analytical testing procedures, either because of the complexity of the analytical procedure and/or the cost of the necessary analytical equipment.

Thus, very commonly, bodyfluid samples are drawn at the physician's office or at smaller laboratories and then shipped frozen with dry ice to larger laboratories where the analytical procedures are performed.

Unfortunately, freezing the bodyfluid only creates a new set of problems in testing the fluid. For example, the sample must be promptly and properly frozen. With blood samples, this first requires centrifuging to remove the red blood cells prior to freezing. During this freezing process, time is of the essence to freeze the sample as promptly as possible. Next, the sample must be shipped with an adequate amount of dry ice to insure that it remains frozen. Once the sample arrives at the testing laboratory, care must be taken to carefully thaw the sample to ensure the integrity of the sample. Generally this requires thawing the sample slowly in an ice water bath. Finally, once the sample is thawed, time is once again of the essence, as the analytical tests must be performed promptly after thawing.

When testing is required to make a determination of, for example, myelin basic protein, parathyroid hormone, adrenocorticotrophic hormone, prostate specific antigen or alpha-fetoprotein, just to name a few, many physician's offices and small laboratories will draw the sample and ship it frozen to a larger laboratory with the ability to perform such desired analytical testing.

For example, U.S. Pat. No. 4,136,160, issued Jan. 23, 1979 to Cohen discloses an assay for active demyelinization. Many diseases and pathologies of the human body are associated with the destruction of myelin, a lipoprotein-rich membrane that surrounds, protects and is critical to neuronal function of the central nervous system. One of the degradation products of demyelinization is a protein known as myelin basic protein. This protein accounts for as much as thirty percent of the protein found in myelin and may be its major structural protein.

One of the major demyelinating diseases suffered by man is multiple sclerosis. In multiple sclerosis, patches of destroyed myelin are replaced by scar tissue that interrupts and distorts the flow of nerve impulses.

The Cohen '160 patent discloses a radioimmunological assay ("RIA") for the detection and measurement of myelin basic protein in cerebrospinal fluid to provide a means for the diagnosing and evaluating the clinical progress of multiple sclerosis and other demyelinating pathologies. It is very clearly taught in Cohen '160 that the cerebrospinal fluid must be tested immediately or stored frozen until assay.

To prevent clotting, either ethylenediamine tetraacetic acid or citric acid salts, both metalo-peptidase inhibitors, are sometimes added to blood.

As the foregoing illustrates, there is a need in the art for a method of processing bodyfluids that will allow for longer time periods between the drawing of the bodyfluid and the analytical testing of such bodyfluids.

This is also a need in the art for a method of processing bodyfluids that will allow for longer time periods in the freezing and thawing of samples to be frozen.

These and other needs will become apparent to those of skill in the art by the following description of the invention.

Thus, it is an object of the present invention to provide a composition useful in the processing of bodyfluids and in the analytical testing of bodyfluids.

It is another object of the present invention to provide a method of processing bodyfluids and of testing bodyfluids.

It is yet another object of the present invention to provide an apparatus useful in the processing and analytical testing of bodyfluids.

It is still yet another object of the present invention to provide for products made from bodyfluids.

It is even still yet another object of the present invention to provide an improved method of analyzing bodyfluids for adrenocorticotrophic hormone, alkaline phosphatase isoenzymes, alpha-fetoprotein, atrial natriuretic factor, c-reactive protein, calcitonin, carbohydrate antigen 19-9, carcinoembryonic antigen, cerebrospinal fluid IgG index, ceruloplasmin, follicle stimulating hormone, gastrin, interleukins, myelin basic protein, parathyroid hormone, parathyroid-related hormone, prolactin, prostate-specific antigen, protein c antigen, ristocetin co-factor plasma, ristocetin inhibitor assay screen, thyroid stimulating hormone, or vasoactive intestinal polypeptide.

These objects and other objects of the present invention will become more apparent to those of skill in the art by the following description of the invention.

SUMMARY OF THE INVENTION

According to one embodiment of the present invention there is provided a composition for processing bodyfluids. The composition of the present invention suitable for use in processing bodyfluids is comprised of a first enzyme inhibitor selected from the group of enzyme inhibitors consisting of inhibitors which allow substantially the function of metalo-peptidase while inhibiting at least one enzyme selected from the group of enzymes consisting of endopeptidase, exopeptidase and sulfhydryl-mediated proteases, and consisting of inhibitors which substantially inhibit the function of metalo-peptidase, wherein where the first enzyme inhibitor inhibits metalo-peptidase, the composition further comprises a second enzyme inhibitor suitable to inhibit at least one enzyme selected from the group of enzymes consisting endopeptidase, exopeptidase, metalo-peptidase and sulfhydryl-mediated proteases.

According to another embodiment of the present invention there is provided a product comprising blood and a first enzyme inhibitor selected from the group of enzyme inhibitors consisting of inhibitors which allow substantially the function of metalo-peptidase while inhibiting at least one enzyme selected from the group of enzymes consisting of endopeptidase, exopeptidase and sulfhydryl-mediated proteases, and consisting of inhibitors which substantially inhibit the function of metalo-peptidase, wherein where the first enzyme inhibitor inhibits metalo-peptidase, the composition further comprises a second enzyme inhibitor suitable to inhibit at least one enzyme selected from the group of enzymes consisting endopeptidase, exopeptidase, metalo-peptidase and sulfhydryl-mediated proteases.

According to yet another embodiment of the present invention there is provided a product comprising cerebrospinal fluid and a first enzyme inhibitor selected from the group of enzyme inhibitors consisting of inhibitors which allow substantially the function of metalopeptidase while inhibiting at least one enzyme selected from the group of enzymes consisting of endopeptidase, exopeptidase and sulfhydryl-mediated proteases, and consisting of inhibitors which substantially inhibit the function of metalo-peptidase, wherein where the first enzyme inhibitor inhibits metalo-peptidase, the composition further comprises a second enzyme inhibitor suitable to inhibit at least one enzyme selected from the group of enzymes consisting endopeptidase, exopeptidase, metalo-peptidase and sulfhydryl-mediated proteases.

According to still another embodiment of the present invention there is provided an apparatus for processing bodyfluids. The apparatus includes a support member and an inhibitor means supported by the support member for either inhibiting exopeptidase, endopeptidase and sulfhydryl-mediated proteases while allowing substantially the action of metalo-peptidase or inhibiting metalo-peptidase. Where the inhibitor means inhibits metalo-peptidase, the apparatus includes a second inhibitor means supported by the support member for inhibiting exopeptidase, endopeptidase, metalo-peptidase or sulfhydryl-mediated peptidase. One embodiment of this apparatus includes a tube containing the inhibitors into which the bodyfluid is added. Another embodiment of this apparatus includes a swizzle stick, plastic bead or other solid phase carrying the inhibitors which is contacted with the drawn bodyfluid sample.

According to still yet another embodiment of the present invention there is provided a method for processing bodyfluids in which the bodyfluid is contacted with the composition of the present invention.

According to even another embodiment of the present invention, there is provided a method for processing bodyfluids. First, the bodyfluid is contacted with the composition of the present invention. Next, the mixture is frozen. Finally, at the time of assay the mixture is then thawed.

According to even yet another embodiment of the present invention there is provided a method for processing bodyfluids in which the bodyfluid is first contacted with the composition of the present invention. Next, the mixture is cooled.

According to additional embodiments of the present invention, there are provided improvements in the assay methods for assaying for such analytes as adrenocorticotrophic hormone, alkaline phosphatase isoenzymes, alpha-fetoprotein (amniotic or spinal fluid), atrial natriuretic factor, c-reactive protein, calcitonin, carbohydrate antigen 19-9, carcinoembryonic antigen, cerebrospinal fluid IgG index, ceruloplasmin, follicle stimulating hormone, gastrin, interleukins, myelin basic protein, parathyroid hormone, parathyroid-related hormone, prolactin, prostate-specific antigen, protein c antigen, ristocetin co-factor plasma, ristocetin inhibitor assay screen, thyroid stimulating hormone, tumor necrosis factor or vasoactive intestinal polypeptide. The improvements comprise contacting the bodyfluid to be analyzed with the composition of the present invention prior to conducting the specific assay.

These embodiments and other embodiments of the present invention will become more apparent to those of skill in the art by the following description of the invention.

BRIEF DESCRIPTION OF THE DRAWINGS

FIG. 1 is a Venn diagram of the four types of enzymes, endopeptidase 30, exopeptidase 40, metaloproteases 34 and sulfhydryl-mediated proteases 32.

FIG. 2 illustrates one embodiment of the apparatus of the present invention comprising supporting member 10, shown as a tube or test tube, and inhibitors 20.

FIG. 3 illustrates another embodiment of the present invention comprising support member 12, shown as a stick or porous member, and inhibitors 15.

DETAILED DESCRIPTION OF THE INVENTION

Enzymes are categorized into four classes of enzymes depending upon their enzymatic mechanism as follows, endopeptidase, exopeptidase, metalo-peptidase and sulfhydryl-mediated proteases.

Referring now to FIG. 1 there is shown is a Venn diagram of the four types of enzymes, endopeptidase 30, exopeptidase 40, metalo-proteases 34 and sulfhydryl-mediated proteases 32.

Generally, the composition of the present invention suitable for use in processing bodyfluids is comprised of a first enzyme inhibitor selected from the group of enzyme inhibitors consisting of inhibitors which allow substantially the function of metalo-peptidase while inhibiting at least one enzyme selected from the group of enzymes consisting of endopeptidase, exopeptidase and sulfhydryl-mediated proteases, and inhibitors which substantially inhibit the function of metalo-peptidase, wherein where the first enzyme inhibitor inhibits metalo-peptidase, the composition further comprises a second enzyme inhibitor suitable to inhibit at least one enzyme selected from the group of enzymes consisting of endopeptidase, exopeptidase, metalo-peptidase and sulfhydryl-mediated proteases.

While it is understood that the first enzyme inhibitor may somewhat inhibit metalo-peptidase enzymes, it must not substantially inhibit the action of such enzymes but must be suitable to substantially allow the action of such enzymes.

The selection of the inhibitors of the present invention is very much dependent upon the analyte in the bodyfluid which is to be measured. The inhibitors selected must not interfere substantially with the analyte analysis and must prevent enzymes in the bodyfluid from substantially altering the analyte.

Preferably, the composition of the present invention suitable for use in processing bodyfluids is comprised of at least two inhibitors wherein the at least two inhibitors together are suitable to inhibit at least two enzymes selected from the group of enzymes consisting of endopeptidase, exopeptidase, metalo-peptidase and sulfhydryl-mediated proteases.

More preferably, the composition of the present invention suitable for use in processing bodyfluids is comprised of at least three inhibitors wherein the at least three inhibitors together are suitable to inhibit at least three enzymes selected from the group of enzymes consisting of endopeptidase, exopeptidase, metalo-peptidase and sulfhydryl-mediated proteases.

Most preferably, the composition of the present invention suitable for use in processing bodyfluids is comprised of at least three inhibitors wherein the at least three inhibitors are suitable to inhibit endopeptidase, exopeptidase, metalo-peptidase and sulfhydryl-mediated proteases.

Since in some instances one inhibitor may inhibit more than one type of enzyme, or N number of enzymes together may inhibit more than N types of enzymes, it is not necessary to have one inhibitor for each type of enzyme. For example, N-tosyl-lysyl chloromethylketone ("TLCK") and N-tosyl-phenylalanyl chloromethylketone ("TPCK") each alone inhibit both endopeptidase and exopeptidase, and acting together additionally inhibit sulfhydryl-mediated proteases.

Suitable endopeptidase inhibitors for use in the present invention include, for example: alkylating agents containing halogen, sulfonate leaving groups or active ketones, for example halogen substituted acetamides, N-tosyl-lysyl chloromethylketone ("TLCK") or N-tosyl-phenylalanyl chloromethylketone ("TPCK"); carboxylating agents activated by treatment with carbodiimides such as acetic acid or maleic acid; chelating agents such as ethylenediamine tetraacetic acid ("EDTA") or ethylene glycol-bis- (beta-aminoethyl)N,N,N',N'-tetraacetic acid ("EGTA"); active sulfonic or phosphoric acid derivatives such as organic sulfonyl or phosphoryl fluorides; peptide inhibitors such as aprotinin, antipain or leupeptin; phosphorylating agents such as fluorophosphates, nitrating agents such as organo nitrates; chaotropic agents; neutral, cationic and anionic detergents; peptides or other agents which have an affinity for the active site for endopeptidase; peptides or other agents that bind to an allosteric site that renders endopeptidase inactive; and organic epoxides.

Preferably, endopeptidase inhibitors suitable for use in the present invention include, for example: TLCK; TPCK; iodo-, chloro- or bromo- acetamides; EDTA; EGTA; aryl or alkyl sulfonyl fluorides; aryl or alkylphosphoryl fluorides; aprotinin; leupeptin; and aryl or alkyl epoxides.

More preferably, endopeptidase inhibitors suitable for use in the present invention include, for example: TLCK; TPCK; iodoacetamide; EDTA; EGTA; phenylmethyl sulfonyl fluoride; aprotinin; and butyl epoxide.

Most preferably, endopeptidase inhibitors suitable for use in the present invention, for example: TLCK; TPCK; and EDTA.

Suitable exopeptidase inhibitors useful in the present invention include, for example: alkylating agents; competitive peptides; lactones such as ebelactone; enzyme product inhibitors such as amino acids including leucine or glycine; chelating or coordinating agents such as EDTA; alkylating agents directed to sulfhydryl, lysyl and histidyl side chain groups or other chemically active moieties of exopeptidase including organo imines such as alkylimines, e.g., ethylene imine; competitive peptides or other agents having an affinity for the active sites of exopeptidase including polyarginine; peptides or other agents that bind to an allosteric site that renders exopeptidase inactive.

Preferably, the exopeptidase inhibitors utilized in the present invention include chelating agents; alkylating agents; EDTA; ethylene imine and polyarginine.

Most preferably, the exopeptidase inhibitors utilized in the present invention include EDTA.

Suitable metalo-peptidase inhibitors useful in the present invention include, for example: ethylenediamine tetraacetic acid ("EDTA"); ethylene glycol-bis-(beta-aminoethyl)N,N,N',N'-tetraacetic acid ("EGTA"); sodium or potassium citrate salts; sodium or potassium oxatate salts; quinoline and its derivatives; deferoxamine and feroxamine-type chelating agents; dithiocarb salts; penicillamines; pentetic salts; succinic; trientine; chelating agents; inhibitory heavy metals and salts thereof, including cobalt, lead, iron and salts thereof; alkylating and carboxylating agents containing, for example, organo-halogen, organo-sulfonate leaving groups or active ketones or carboxylic acids activated by treatment with carbodiimides; phosphorylating agents such as diisopropyl fluorophosphate and nitrating agents such as tetranitromethane which affect inhibition by altering the metallic mediated catalysis; peptides or other agents that bind to an allosteric site that renders metalo-peptidase inactive.

Preferably, the metalo-peptidase inhibitors utilized in the present invention include EDTA, EGTA, quinoline and derivatives of quinoline.

Most preferably, the metalo-peptidase inhibitors utilized in the present invention include EDTA and EGTA.

Suitable sulfhydryl-mediated protease inhibitors include, for example, EDTA, thiols, benzoates, halogen substituted acetic acid, halogen substituted acetamides, metals salts such as mercury or copper salts, and alkylating agents such as TLCK and TPCK.

Preferably, sulfhydryl-mediated protease inhibitors utilized in the present invention include, for example, TLCK, TPCK, hydroxymercurobenzoate, iodoacetic acid and iodoacetamide.

Most preferably, the sulfhydryl-mediated protease inhibitors utilized in the present invention include EDTA, TLCK and TPCK.

Suitable combinations of inhibitors which will inhibit sulfhydryl-mediated proteases include combinations of TLCK, TPCK, cystine, copper salts and hydroxymercurobenzoate.

A preferred composition of the present invention comprises EDTA and at least one of TLCK and TPCK. A more preferred composition of the present invention comprises EDTA, TLCK and TPCK.

The composition of the present invention may be utilized in any physical form. For example, the composition may be utilized as a solution in a test tube, or may be utilized in a solid form deposited in a test tube.

Solvents which may be utilized with the composition of the present invention generally include any solvent capable of solubilizing the composition and which will not substantially interfere with the collection of the bodyfluid and the subsequent analysis. Preferably, polar solvents, for example water, organic solvents, or combinations thereof are utilized in the present invention.

For example, EDTA is not readily soluble in ethanol. TPCK is not readily soluble in water. Therefore, to create a solution, EDTA is first neutralized in water, TPCK and TLCK are both first solubilized in ethanol, with the resulting solutions combined to form a solubilized mixture of the composition.

The bodyfluid processing method of the present invention includes the step of contacting the bodyfluid with the inhibitors to yield a product comprising the bodyfluid and inhibitors. This product is suitable for analytical testing. The inhibitor composition of the present invention is generally contacted with the bodyfluid sample promptly after the sample is drawn.

Where the analytical testing cannot be conducted within a reasonable amount of time, it is then preferable, although not necessary, that the inhibitors of the present invention be utilized in conjunction with refrigeration or freezing. For example, drawn blood or cerebrospinal fluid samples are first contacted with the inhibitors of the present invention, cellular components are removed, and the remaining portion of the sample then refrigerated or frozen.

In the practice of the present invention, the contacted mixture of the inhibitors and the bodyfluid will generally comprise amounts of inhibitors suitable so that the bodyfluids can be subjected to effective diagnostic examination. There must be at least a sufficient amount of inhibitor to substantially preserve the analyte. At the upper limit, the amount of inhibitor must not interfere with effective diagnostic examination of the analyte. In practical terms, the upper limit is generally the solubility limit for the inhibitor in the bodyfluid, which is generally further tempered by any economic considerations.

Generally, this means that the contacted mixture of the inhibitors and the bodyfluid will generally comprise for each class of inhibitor a concentration in the range of about $10^{-7}$ moles inhibitor/liter of mixture to about $10^{-2}$ moles inhibitor/liter of mixture. Preferably the concentration will comprise in the range of about $10^{-5}$ moles inhibitor/liter of mixture to about $10^{-3}$ moles inhibitor/liter of mixture, and most preferably the concentration will comprise in the range of about $10^{-5}$ moles inhibitor/liter of mixture to about $10^{-4}$ moles inhibitor/liter of mixture.

The apparatus of the present invention generally includes a supporting member for supporting the inhibitors.

Referring now to FIG. 2 there is illustrated one embodiment of the apparatus of the present invention comprising supporting member 10, shown as a tube or test tube, and inhibitors 20. The bodyfluid sample may be drawn and then placed in tube 10. Alternatively, tube 10 may be sealed under vacuum, with the bodyfluid drawn directly into tube 10.

Referring now to FIG. 3, there is illustrated another embodiment of the apparatus of the present invention comprising support member 12, shown as a stick or porous member, and inhibitors 15. Inhibitors 15 are supported by member 12 and my in, on, around, affixed to or dried upon member 12. In operation, the sample is drawn into a tube and this wooden stick added to the sample, or the sample is first placed in a tube with the bodyfluid sample then added to the tube.

Once the bodyfluid has been contacted with the inhibitor composition of the present invention, it may be subjected to analytical testing. Such testing includes assaying techniques including, for example, radioimmunoassay and enzyme linked immunoassay.

In the practice of the present invention, analytical tests that may be performed after contacting the bodyfluid with the inhibitors include tests for hormones in general, pituitary hormones, cancer markers and bacterial proteins. Specific examples include tests for adrenocorticotrophic hormone, alkaline phosphatase isoenzymes, alpha-fetoprotein (amniotic or spinal fluid), atrial natriuretic factor, c-reactive protein, calcitonin, carbohydrate antigen 19-9, carcinoembryonic antigen, cerebrospinal fluid IgG index, ceruloplasmin, follicle stimulating hormone, gastrin, interleukins, myelin basic protein, parathyroid hormone, parathyroidrelated hormone, prolactin, prostate-specific antigen, protein c antigen, ristocetin co-factor plasma, ristocetin inhibitor assay screen, thyroid stimulating hormone, tumor necrosis factor or vasoactive intestinal polypeptide.

EXAMPLES

The following examples are provided to illustrate embodiments of the present invention and to help in the understanding of the present invention. The present invention is not intended to be and is not limited by the following examples.

Example 1

This example compares test results for levels of parathyroid hormone ("PTH") at the time of sampling, after three and six days of freezing and after three and six days utilizing the teachings of the present invention.

Human blood samples were taken and with each sample divided into 5 groups for initial testing, three day testing with inhibitors and freezing, and six day testing with inhibitors and freezing.

Initial tests were conducted promptly upon drawing the blood sample.

For the inhibitor samples, an inhibitor composition was promptly added and the inhibitor samples kept at an approximate room temperature of 22° C. until testing at the three and six day mark. The inhibitor composition comprised TLCK, TPCK and EDTA. Final dilution in blood was about $10^{-4}$ moles of each inhibitor/liter of blood.

For the frozen sample, the blood was promptly centrifuged to remove red blood cells and then frozen in a dry ice/methanol bath. The samples were thawed in about an hour in an ice water bath for testing at the three and six day mark.

Analysis was by radioimmunoassay (Parathyroid Hormone Assay Kit from Nichols Laboratory, Inc.) with a double antibody method for precipitating the immune complex. Standards were provided with the kit. Known bio-rad controls were utilized to validate the results.

TABLE I

Results of PTH Testing With Inhibitors

| Sample Number | Initial Test | After 3 Days | | After 6 Days | |
|---|---|---|---|---|---|
| | | Freeze W/Thaw | Inhibitors Only | Freeze W/Thaw | Inhibitors Only |
| 1 | 154 | | | 61 | 123 |
| 2 | 106 | | | 34 | 36 |
| 3 | 89 | | | 11 | 36 |
| 4 | 115 | 60 | 97 | 2 | 34 |
| 5 | 98 | | | 20 | 49 |
| 6 | 81 | | | 67 | 43 |
| 7 | 65 | 30 | 59 | 18 | 46 |
| 8 | 68 | | | 44 | 31 |
| 9 | 252 | 90 | 192 | 45 | 48 |

Referring now to Table I which shows the results for this example, it can been seen that the inhibitors of the present invention maintain the integrity of the sample better than the freezing technique for both the three day and six day intervals.

Example 2

The example compares myelin basic protein ("MBP") levels after three days for samples without freezing or inhibitors, for samples with inhibitors, and for samples which are frozen with inhibitors.

Human cerebrofluid samples were taken and with each sample divided into three groups for testing without freezing or inhibitors, for testing with inhibitors, and for testing with freezing and inhibitors.

The samples without inhibitors or freezing were kept at an approximate temperature of 37° for 72 hours until testing.

For the inhibitor samples, an inhibitor composition was promptly added and the inhibitor samples kept at an approximate temperature of 37° C. until testing after 72 hours. The inhibitor composition comprised TLCK, TPCK and EDTA. Final dilution in the cerebrospinal fluid was about $10^{-4}$ moles of each inhibitor/liter of fluid.

For the frozen sample, an inhibitor composition was promptly added with the sample then frozen in a dry ice/methanol bath. The samples were thawed in about an hour in an ice water bath for testing at the 72 hour mark.

Analysis was by radioimmunoassay (MBP Assay Kit from Biotecx, Inc.) with a double antibody method for precipitating the immune complex. The immune complex standards and known controls were provided with the kit. Known bio-rad controls were utilized to validate the results.

TABLE II

Analysis of Inhibitors On Spinal Fluid For Myelin Basic Protein Levels

| Test Number | No PIT | With Pit | Frozen + PIT |
|---|---|---|---|
| 1 | 0.4 | 1.2 | 0.9 |
| 2 | 0.4 | 0.9 | 1.1 |
| 3 | 0.4 | 1 | 1.1 |
| 4 | 0.2 | 1.1 | 1 |
| 5 | 3.6 | 8.5 | 9.1 |
| 6 | 4.3 | 8.6 | 10 |
| 7 | 3.6 | 8.7 | 10.8 |
| 8 | 3.4 | 9.4 | 9.7 |
| 9 | 5.8 | 10.3 | 11.9 |
| 10 | 5.1 | 10.9 | 11.3 |
| 11 | 4.7 | 11.6 | 11.3 |
| 12 | 5.5 | 11.3 | 11.5 |

Referring now to Table II, results of MBP levels are presented after 72 hours for samples with no inhibitors or freezing, for samples with inhibitors only, and for samples frozen with inhibitors.

I claim:

1. A product comprising blood, ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the product.

2. The product of claim 1 wherein the ethylenediamine tetraacetic acid and the at least one compound each comprise in the range of about $10^{-7}$ to about $10^{-2}$ moles per liter of the product.

3. The product of claim 1 comprising ethylenediamine tetraacetic acid, N-tosyl-lysyl chloromethylketone and N-tosyl-phenylalanyl chloromethylketone.

4. The product of claim 3 wherein the ethylenediamine tetraacetic acid, N-tosyl-lysyl chloromethylketone and N-tosyl-phenylalanyl chloromethylketone each comprise in the range of about $10^{-7}$ to about $10^{-2}$ moles per liter of the product.

5. A product comprising cerebrospinal fluid, ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the product.

6. The product of claim 5 wherein the ethylenediamine tetraacetic acid and the at least one compound each comprise in the range of about $10^{-7}$ to about $10^{-2}$ moles per liter of the product.

7. The product of claim 5 comprising ethylenediamine tetraacetic acid, N-tosyl-lysyl chloromethylketone and N-tosyl-phenylalanyl chloromethylketone.

8. The product of claim 7 wherein the ethylenediamine tetraacetic acid, N-tosyl-lysyl chloromethylketone and N-tosyl-phenylalanyl chloromethylketone each comprise in the range of about $10^{-7}$ to about $10^{-2}$ moles per liter of the product.

9. A processing method for processing bodyfluids comprising contacting the bodyfluid with a processing composition to form a processed product, wherein the processing composition comprises ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the processed product.

10. The method of claim 9 wherein the processing composition comprises ethylenediamine tetraacetic acid, N-tosyl-lysyl chloromethylketone and N-tosyl-phenylalanyl chloromethylketone.

11. The method of claim 10 further comprising analytically testing the processed product.

12. The method of claim 10 further comprising freezing the processed product to form a frozen product.

13. The method of claim 12 further comprising thawing the frozen product to form a thawed product.

14. The method of claim 13 further comprising analytically testing the thawed product.

15. A freezing method for freezing bodyfluids comprising contacting the bodyfluid with a freezing composition, and freezing to form a frozen product, wherein the freezing composition comprises ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the frozen product.

16. The method of claim 15 wherein the freezing composition comprises, ethylenediamine tetraacetic acid, N-tosyl-lysyl chloromethylketone and N-tosyl-phenylalanyl chloromethylketone.

17. A method for freezing bodyfluids comprising:
(a) contacting the bodyfluid with a composition to form a freezable product, wherein the composition comprises ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the freezable product; and
(b) freezing the freezable product of step (a) to form a frozen product.

18. The method of claim 17 wherein the bodyfluid is contacted with a composition comprising ethylenediamine tetraacetic acid, N-tosyl-lysyl chloromethylketone and N-tosyl-phenylalanyl chloromethylketone.

19. The method of claim 17 further comprising:
(c) thawing the frozen product of step (b) to form a thawed product.

20. The process of claim 19 further comprising:
(d) assaying the thawed product of step (c).

21. A method for cooling bodyfluids comprising:
(a) contacting the bodyfluid with a composition to form a product, wherein the composition comprises ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the product; and
(b) cooling the product of step (a) to form a cooled product.

22. The method of claim 21 wherein the bodyfluid is contacted with a composition comprising ethylenediamine tetraacetic acid, N-tosyl-lysyl chloromethylketone and N-tosyl-phenylalanyl chloromethylketone.

23. The method of claim 21 further comprising:
(c) assaying the cooled product of step (b).

24. The method of claim 21 further comprising:
(c) freezing the cooled product of step (b) to form a frozen product.

25. The method of claim 24 further comprising:
(d) thawing and then assaying the frozen product of step (c).

26. A method for preparing bodyfluids for assaying for a desired analyte comprising:

(a) contacting the bodyfluid with a composition to form a product, wherein the composition comprises ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the product.

27. The method of claim 26 wherein the bodyfluid is contacted with a composition comprising ethylenediamine tetraacetic acid, N-tosyl-lysyl chloromethylketone and N-tosyl-phenylalanyl chloromethylketone.

28. The method of claim 27 wherein the analyte is myeline basic protein or parathyroid hormone.

29. The process of claim 26 wherein step the analyte is selected from the group of analytes consisting of adrenocorticotrophic hormone, alkaline phosphatase isoenzymes, alpha-fetoprotein (maternal serum or spinal fluid), atrial natriuretic factor, c-reactive protein, calcitonin, carbohydrate antigen 19-9, carcinoembryonic antigen, cerebrospinal fluid IgG index, ceruloplasmin, follicle stimulating hormone, gastrin, interleukins, myelin basic protein, parathyroid hormone, parathyroid-related hormone, prolactin, prostate-specific antigen, protein c antigen, ristocetin co-factor, ristocetin inhibitor, thyroid stimulating hormone, tumor necrosis factor or vasoactive intestinal polypeptide.

30. A method for assaying bodyfluids for a desired analyte comprising contacting together the bodyfluid, an antibody which specifically binds the analyte, and a composition comprising ethylenediamine tetraacetic acid and at least one compound selected from the group consisting of N-tosyl-lysyl chloromethylketone and N-tosyl-phenylalanyl chloromethylketone in amounts sufficient to inhibit endopeptidases in the bodyfluid; and detecting bound antibody.

31. The method of claim 30 wherein the composition comprises ethylenediamine tetraacetic acid, N-tosyl-lysyl chloromethylketone and N-tosyl-phenylalanyl chloromethylketone.

32. In the method of analyzing a bodyfluid for myeline basic protein which comprises the step of contacting an antibody which specifically binds myelin basic protein with the bodyfluid and detecting bound antibody, wherein the improvement comprises contacting together the antibody, the bodyfluid, and an assaying composition comprising ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the bodyfluid.

33. The method of claim 32 wherein the assaying composition comprises ethylenediamine tetraacetic acid, N-tosyl-lysyl chloromethylketone and N-tosyl-phenylalanyl chloromethylketone.

34. In the method of analyzing a bodyfluid and adrenocorticotrophic hormone which comprises the step of contacting an antibody which specifically binds adrenocorticotrophic hormone with the bodyfluid and detecting bound antibody, wherein the improvement comprises contacting together the antibody, the bodyfluid, and an assaying composition comprising ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the bodyfluid.

35. The method of claim 34 wherein the assaying composition comprises ethylenediamine tetraacetic acid, N-tosyl-lysyl chloromethylketone and N-tosyl-phenylalanyl chloromethylketone.

36. In the method of analyzing a bodyfluid for adrenocorticotrophic hormone which comprises the step of contacting an antibody which specifically binds alpha-fetoprotein with the bodyfluid and detecting bound antibody, wherein the improvement comprises contacting together the antibody, the bodyfluid, and an assaying composition comprising ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the bodyfluid.

37. The method of claim 36 wherein the assaying composition comprises ethylenediamine tetraacetic acid, N-tosyl-lysyl chloromethylketone and N-tosyl-phenylalanyl chloromethylketone.

38. In the method of analyzing a bodyfluid for prostate-specific antigen which comprises the step of contacting an antibody which specifically binds prostate-specific antigen with the bodyfluid and detecting bound antibody, wherein the improvement comprises contacting together the antibody, the bodyfluid, and an assaying composition comprising ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the bodyfluid.

39. The method of claim 110 wherein the assaying composition comprises ethylenediamine tetraacetic acid, N-tosyl-lysyl chloromethylketone and N-tosyl-phenylalanyl chloromethylketone.

40. In the method of analyzing a bodyfluid for adrenocorticotrophic hormone which comprises the step of contacting an antibody which specifically binds parathyroid hormone with the bodyfluid and detecting bound antibody, wherein the improvement comprises contacting together the antibody, the bodyfluid, and an assaying composition comprising ethylenediamine tetraacetic acid and at least one compound selected from the group of compounds consisting of N-tosyl-lysyl chloromethylketone and N-tosyl-phenylalanyl chloromethylketone in amounts sufficient to inhibit endopeptidases in the bodyfluid.

41. The method of claim 40 wherein the assaying composition comprises ethylenediamine tetraacetic acid, N-tosyl-lysyl chloromethylketone and N-tosyl-phenylalanyl chloromethylketone.

42. The method of claim 26 further comprising:
(b) contacting the product of step (a) with an antibody which specifically binds the desired analyte to form an analyte-antibody complex; and
(c) detecting the analyte-antibody complex.

43. The method of claim 27 further comprising:
(b) contacting the product of step (a) with an antibody which specifically binds the desired analyte to form an analyte-antibody complex; and
(c) detecting the analyte-antibody complex.

44. The method of claim 28 further comprising:
(b) contacting the product of step (a) with an antibody which specifically binds the desired analyte to form an analyte-antibody complex; and
(c) detecting the analyte-antibody complex.

* * * * *